(12) United States Patent
Wang et al.

(10) Patent No.: US 10,167,306 B2
(45) Date of Patent: Jan. 1, 2019

(54) CRYSTALLINE FORM OF 1-(BETA-D-GLUCOPYRANOSYL)-4-METHYL-3-[5-(4-FLUOROPHENYL)-2-THIENYLMETHYL] BENZENE AND PREPARATION METHOD THEREOF

(71) Applicants: SHANGHAI DESANO PHARMACEUTICALS INVESTMENT CO., LTD, Shanghai (CN); SHANGHAI DESANO CHEMICAL PHARMACEUTICAL CO., LTD, Shanghai (CN)

(72) Inventors: Meng Wang, Shanghai (CN); Liang Zhang, Shanghai (CN)

(73) Assignees: SHANGHAI DESANO PHARMACEUTICALS INVESTMENT CO., LTD., Shanghai (CN); SHANGHAI DESANO CHEMICAL PHARMACEUTICAL CO., LTD, Shanghai (CN)

( * ) Notice: Subject to any disclaimer, the term of this patent is extended or adjusted under 35 U.S.C. 154(b) by 183 days.

(21) Appl. No.: 15/003,681

(22) Filed: Jan. 21, 2016

(65) Prior Publication Data
US 2016/0222046 A1    Aug. 4, 2016

(30) Foreign Application Priority Data
Feb. 4, 2015   (CN) .......................... 2015 1 0059262

(51) Int. Cl.
C07H 7/04      (2006.01)
C07D 409/10    (2006.01)
A61K 31/381    (2006.01)

(52) U.S. Cl.
CPC ............. *C07H 7/04* (2013.01); *A61K 31/381* (2013.01); *C07D 409/10* (2013.01); *C07B 2200/13* (2013.01)

(58) Field of Classification Search
CPC ................................ C07H 7/04; C07D 409/10
See application file for complete search history.

(56) References Cited

U.S. PATENT DOCUMENTS

| | | | |
|---|---|---|---|
| 2009/0233874 A1 | 9/2009 | Abdel-Magid et al. | |
| 2017/0342061 A1* | 11/2017 | Wang | ................... C07D 409/10 |

FOREIGN PATENT DOCUMENTS

| | | | |
|---|---|---|---|
| CN | 103554092 A | | 2/2014 |
| CN | 103588762 A | | 2/2014 |
| CN | 103936725 A | | 7/2014 |
| CN | 103936726 A | | 7/2014 |
| CN | 103980261 A | | 8/2014 |
| CN | 103980262 A | | 8/2014 |
| CN | 104130246 A | | 11/2014 |
| CN | 104530023 | * | 4/2015 |
| WO | 2008/069327 A1 | | 6/2008 |
| WO | 2013/064909 A2 | | 5/2013 |
| WO | 2014/180872 A1 | | 11/2014 |
| WO | WO2015071761 | * | 5/2015 |

OTHER PUBLICATIONS

Machine translation of CN104530023 (Year: 2015).*

* cited by examiner

*Primary Examiner* — Leigh C Maier
(74) *Attorney, Agent, or Firm* — Mintz, Levin, Cohn, Ferris, Glovsky and Popeo, P.C.

(57) ABSTRACT

The present invention relates to a crystalline form of 1-(β-d-glucopyranosyl)-4-methyl-3-[5-(4-fluorophenyl)-2-thienylmethyl]benzene. Specifically, it discloses a novel crystalline form of 1-(β-d-glucopyranosyl)-4-methyl-3-[5-(4-fluorophenyl)-2-thienylmethyl]benzene and the preparation method as well as use thereof. The novel crystalline form of 1-(β-d-glucopyranosyl)-4-methyl-3-[5-(4-fluorophenyl)-2-thienylmethyl]benzene provided in the present invention has the advantages such as stable physical and chemical properties, high purity, excellent reproducibility and industrial production suitability.

12 Claims, 4 Drawing Sheets

CRYSTALLINE FORM OF 1-(BETA-D-GLUCOPYRANOSYL)-4-METHYL-3-[5-(4-FLUOROPHENYL)-2-THIENYLMETHYL] BENZENE AND PREPARATION METHOD THEREOF

CROSS-REFERENCES TO RELATED APPLICATIONS

This application claims the benefit of priority to Chinese Patent Application No. 201510059262.X, filed Feb. 4, 2015, which is incorporated by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention relates to the field of pharmaceutical chemistry and, particularly, to a crystalline form of 1-(β-D-glucopyranosyl)-4-methyl-3-[5-(4-fluorophenyl)-2-thienylmethyl]benzene and preparation method thereof.

BACKGROUND OF THE INVENTION

Canagliflozin (compound of formula I), chemically named as 1-(β-D-glucopyranosyl)-4-methyl-3-[5-(4-fluorophenyl)-2-thienylmethyl]benzene, is developed by Janssen Pharmaceutical Ltd., a subsidiary of Johnson & Johnson Pharmaceutical Ltd. It was approved by FDA as a hypoglycemic drug for treating type II diabetes on Mar. 29, 2013, and is the first FDA-approved sodium-glucose cotransporter 2 (SGLT2) inhibitor. SGLT2 inhibitors can specifically inhibit glucose uptake of kidney, which allows excess glucose to be excreted in the urine and thus directly reduces blood sugar levels.

I

Up to present, the reported crystalline form of canagliflozin includes a hemihydrate crystalline form of canagliflozin as disclosed in WO2008069327. However, this crystalline form has shortcomings such as small crystalline particles as well as large static electricity, so that there are negative effects on preparation of pharmaceutical formulations.

US2009/0233874A1 disclosed another crystalline form of canagliflozin and a preparation method thereof. However, the appearance of crystal obtained by this method was gray white, while canagliflozin crystals with high purity should be pure white.

CN103554092A disclosed a crystalline form named as form B, and CN103588762A disclosed two crystalline forms named as form C and form D. Form B and form C were acquired by volatilizing organic solvent from a mixed solvent containing 50% of water at room temperature and form D was obtained by heating form C so as to remove the solvent. However, industrial production of above three crystalline forms is difficult to achieve.

CN103980261A, CN103980262A and CN103936725A disclosed another three crystalline forms of canagliflozin named as form A, form B and form C, wherein form A was a crystal with long flake shape and poor liquidity, form B had a poor reproducibility of preparation, and form C had low crystallinity and contained some amorphous form.

CN104130246A disclosed a crystalline form named as form E which also had low crystallinity as well as incomplete crystal transformation and contained some amorphous form.

WO2014/180872A1 disclosed a non-stoichiometric hydrate crystalline form of canagliflozin. Since the water content of this form was non-stoichiometric, the crystalline characteristics also could not be fully determined. It was difficult to ensure preparation of crystalline form with a consistent quality in a large-scale production process.

CN103935726A disclosed form III and form IV of canagliflozin, wherein form III was an octanol solvate while form IV was an anhydrous form. Since octanol is of high boiling point, it is difficult for the residual octanol in form III to meet requirements of pharmacopoeia. Form IV was obtained by pulping form III in n-heptane and then drying in vacuo for 24 hours. The time for in vacuo drying was long because it was required to fully removal of solvent octanol. When products are dried in large quantities in industry, the residual octanol may easily exceed the required limits.

In summary, there is an urgent need in the art to develop a new crystalline form of canagliflozin with high purity, stable physical and chemical properties, excellent reproducibility and industrial production suitability.

BRIEF SUMMARY OF THE INVENTION

One object of the present invention is to provide a new crystalline form of canagliflozin with high purity, stable physical and chemical properties, excellent reproducibility and industrial production suitability.

In the first aspect of the present invention, a crystalline form W of 1-(β-D-glucopyranosyl)-4-methyl-3-[5-(4-fluorophenyl)-2-thienylmethyl]benzene is provided, and an X-ray powder diffraction pattern of the crystalline form W comprises 3 or more 2θ values selected from the group consisting of: 8.3±0.2°, 12.0±0.2°, 15.2±0.2°, 17.4±0.20, 17.9±0.20, and 22.8±0.2°.

In another preferred embodiment, the X-ray powder diffraction pattern of the crystalline form W comprises 3 or more 2θ values selected from the group consisting of: 8.3°, 12.0°, 15.2°, 17.4°, 17.9°, and 22.8°.

In another preferred embodiment, the X-ray powder diffraction pattern of the crystalline form W comprises the following 2θ value: 8.3°, 12.0°, 15.2°, 17.4°, 17.9°, and 22.8°.

In another preferred embodiment, the X-ray powder diffraction pattern of the crystalline form W comprises 6 or more 2θ values selected from the group consisting of: 4.1±0.2°, 8.3±0.2°, 9.6±0.2°, 12.0±0.2°, 12.5±0.2°, 15.2±0.2°, 16.7±0.20, 17.4±0.20, 17.9±0.2°, 20.4±0.2°, 21.5±0.2°, 22.8±0.2°, 24.3±0.2°, and 31.4±0.2°.

In another preferred embodiment, the X-ray powder diffraction pattern of the crystalline form W comprises 6 or more 2θ values selected from the group consisting of: 4.1°, 8.30, 9.60, 12.00, 12.50, 15.20, 16.70, 17.40, 17.90, 20.40, 21.50, 22.80, 24.30, and 31.4°.

Figure 1:
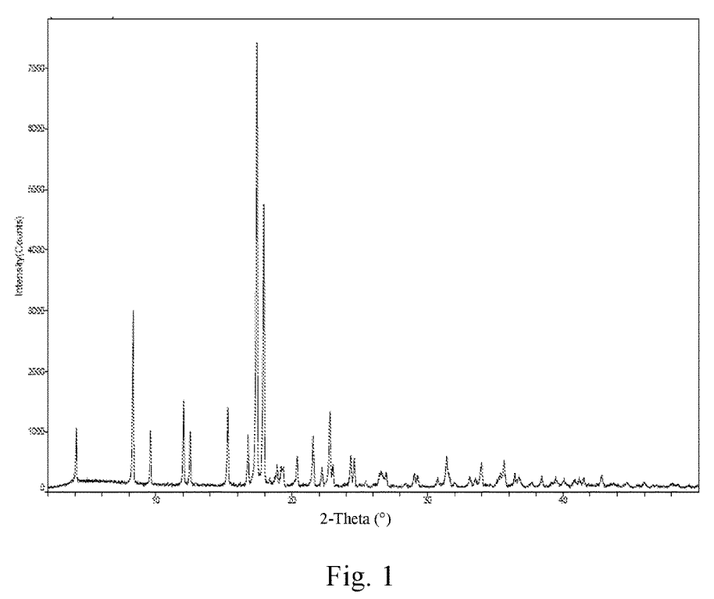
FIG. 1 shows an XRPD pattern of crystalline form W prepared in Example 1 of the present invention.

In another preferred embodiment, the crystalline form W has an X-ray powder diffraction pattern as substantially shown in FIG. 1.

In another preferred embodiment, the 2θ values of the X-ray powder diffraction pattern of the crystalline form W have a deviation of ±0.5, preferably a deviation of ±0.3, and more preferably a deviation of ±0.1.

In another preferred embodiment, the differential scanning calorimetry pattern of the crystalline form W comprises a characteristic peak in the range of 25-200° C. with an onset of approximately 80-90° C.

Figure 2:
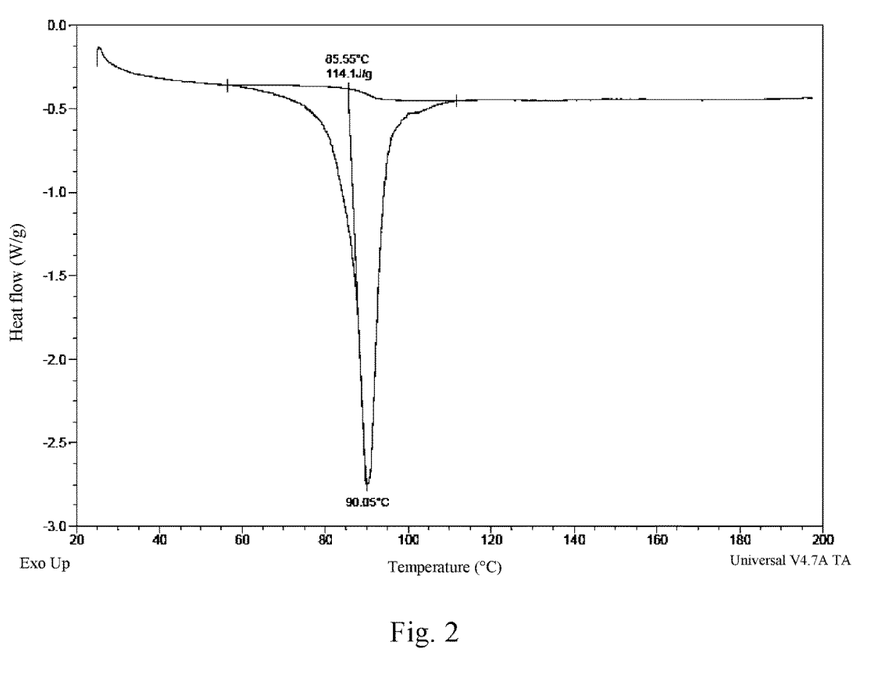
FIG. 2 shows a DSC pattern of crystalline form W prepared in Example 1 of the present invention.

In another preferred embodiment, the crystalline form W has a differential scanning calorimetry pattern as substantially shown in FIG. 2.

In another preferred embodiment, the infrared absorption spectrum of the crystalline form W has characteristic peaks at 3326±2 $cm^{-1}$, 2928±2 $cm^{-1}$, 1647±2 $cm^{-1}$, 1411±2 $cm^{-1}$, 1358±2 $cm^{-1}$, 1323±2 $cm^{-1}$, 1280±2 $cm^{-1}$, 923±2 $cm^{-1}$, 832±2 $cm^{-1}$, 811±2 $cm^{-1}$, 707±2 $cm^{-1}$, 687±2 $cm^{-1}$, and 452±2 $cm^{-1}$.

In another preferred embodiment, the infrared absorption spectrum of the crystalline form W has characteristic peaks at 3326±1 $cm^{-1}$, 2928±1 $cm^{-1}$, 1647±1 $cm^{-1}$, 1411±1 $cm^{-1}$, 1358±1 $cm^{-1}$, 1323±1 $cm^{-1}$, 1280±1 $cm^{-1}$, 923±1 $cm^{-1}$, 832±1 $cm^{-1}$, 811±1 $cm^{-1}$, 707±1 $cm^{-1}$, 687±1 $cm^{-1}$, and 452±1 $cm^{-1}$.

Figure 4:
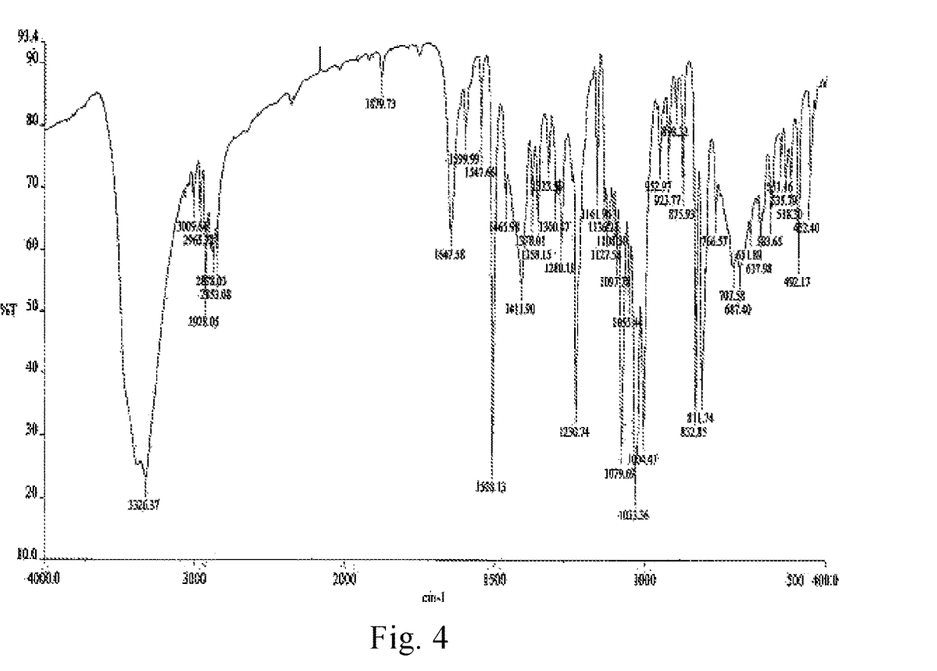
FIG. 4 shows a FTIR pattern of crystalline form W prepared in Example 1 of the present invention.

In another preferred embodiment, the crystalline form W has an FTIR pattern as substantially shown in FIG. 4.

In another preferred embodiment, the TGA pattern of the crystalline form W has about 3.89% of weight loss at 25-100° C.

Figure 3:
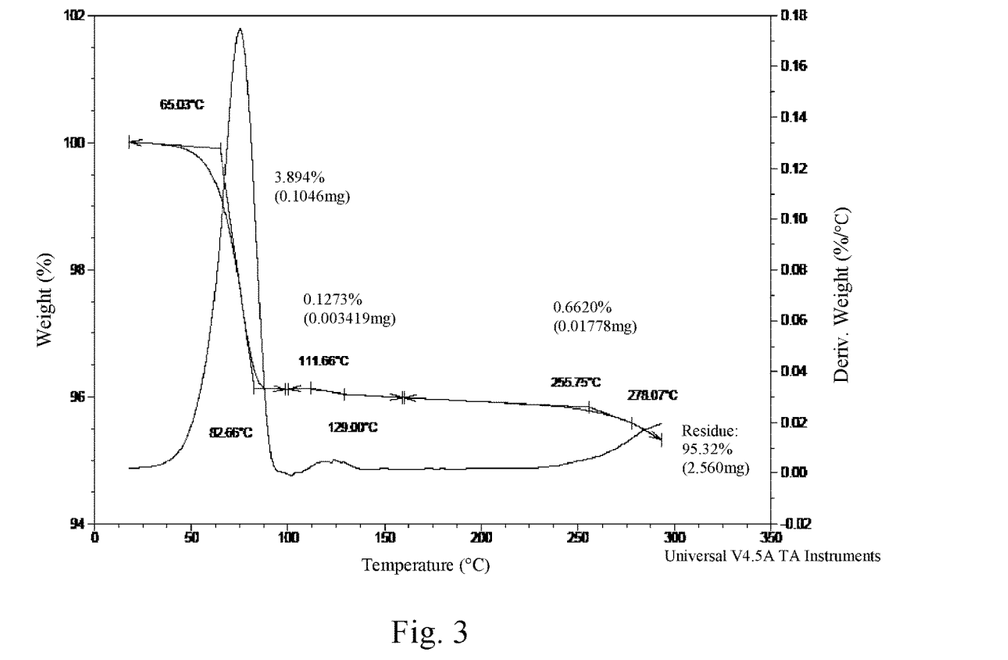
FIG. 3 shows a TGA pattern of crystalline form W prepared in Example 1 of the present invention.

In another preferred embodiment, the crystalline form W has a TGA pattern W as substantially shown in FIG. 3.

In another preferred embodiment, the crystalline form is rodlike.

In the second aspect of the present invention, it provides a method for preparing the crystalline form W in the first aspect of the present invention, comprising the following steps:

a-1) providing a first solution which contains a first solvent and a canagliflozin material dissolved in the first solvent, wherein the first solvent is a good solvent or mixed solvent of the good solvent and water;

wherein the good solvent is selected from the group consisting of: alcohols, ketones, esters, ethylene glycol dimethyl ether, tetrahydrofuran, acetonitrile, dimethylsulfoxide, N-methylpyrrolidone, N,N-dimethylformamide, N,N-dimethylacetamide, or combinations thereof, and a-2) slowly adding the first solution of step a-1) dropwise into a −25 to 50° C. second solvent, thereby crystallizing to obtain the crystalline form W in the first aspect of the present invention, wherein, the second solvent is selected from the group consisting of: water, ethyl ether, isopropyl ether, petroleum ether, methyl tert-butyl ether, n-hexane, cyclohexane, n-pentane, n-heptane, or combinations thereof.

In another preferred embodiment, the alcohol is C1-C10 alcohol, preferably C1-C6 alcohol, and more preferably C1-C3 alcohol.

In another preferred embodiment, the alcohol is selected from the group consisting of: methanol, ethanol, isopropanol, or combinations thereof.

In another preferred embodiment, the alcohol is preferably isopropanol.

In another preferred embodiment, the ketone is C2-C8 ketone, preferably C3-C5 ketone, and preferably acetone.

In another preferred embodiment, the ester is C2-C10 ester, preferably C3-C7 ester, and more preferably ethyl acetate.

In another preferred embodiment, the first solvent is a mixed solvent of a good solvent and water.

In another preferred embodiment, the volume ratio of the good solvent to water is 1-30:1, preferably 1-20:1, and more preferably 1-10:1.

In another preferred embodiment, in the first solution, the concentration of canagliflozin is 0.01-5 g/ml, preferably 0.01-2 g/ml, and more preferably 0.05-0.5 g/ml.

In another preferred embodiment, the canagliflozin material is dissolved in the first solvent at 20-80° C.

In another preferred embodiment, before step a-2), it further comprises the following step:

a-11) filtering insoluble substance from the first solution.

In another preferred embodiment, the filtering in step a-11) is filtering by using a nylon film.

In another preferred embodiment, the pore size of the nylon film is 0.1-1 um, preferably 0.1-0.5 um, and more preferably 0.45 um.

In another preferred embodiment, the volume ratio of the second solvent to the first solvent is 1-5:5-1, preferably 1-5:1, and more preferably 1-4:1.

In the third aspect of the present invention, it provides a method for preparing the crystalline form W in the first aspect of the present invention, comprising the following steps:

b-1) dissolving the canagliflozin material in a third solvent to give a second solution, wherein, the third solvent is a mixed solvent of a good solvent and water, or a mixed solvent of good solvent and poor solvent and water;

the good solvent is selected from the group consisting of: alcohols, ketones, esters, dimethyl sulfoxide (DMSO), N-methylpyrrolidone, tetrahydrofuran, acetonitrile, N,N-dimethylformamide, N,N-dimethylacetamide, ethylene glycol dimethyl ether, or combinations thereof;

the poor solvent is selected from the group consisting of: ethyl ether, isopropyl ether, petroleum ether, methyl tert-butyl ether, n-hexane, cyclohexane, n-pentane, n-heptane, chloralkane, or combinations thereof; and b-2) adding the crystalline form W seed obtained in the present invention into the second solution, thereby crystallizing to obtain the crystalline form W in the first aspect of the present invention.

In another preferred embodiment, the alcohol is C1-C10 alcohol, preferably C1-C6 alcohol, and more preferably C1-C3 alcohol.

In another preferred embodiment, the alcohol is selected from the group consisting of: methanol, ethanol, isopropanol, or combinations thereof.

In another preferred embodiment, the ketone is C2-C8 ketone, preferably C3-C5 ketone, and preferably acetone.

In another preferred embodiment, the ester is C2-C10 ester, preferably C3-C7 ester, and preferably ethyl acetate.

In another preferred embodiment, the chloralkane is methylene chloride or chloroform, and preferably methylene chloride.

In another preferred embodiment, the third solvent is a mixed solvent of a good solvent and water.

In another preferred embodiment, the volume ratio of the good solvent to water is 1-50:5-1, preferably 1-30:3-1, and more preferably 1-10:1.

In another preferred embodiment, the third solvent is a mixed solvent of a good solvent, a poor solvent and water.

In another preferred embodiment, in the third solvent, the volume ratio of (the good solvent+the poor solvent) to water is 1-50:5-1, preferably 1-30:3-1, and more preferably 1-10:1.

In another preferred embodiment, in the second solution, the concentration of canagliflozin is 0.05-5 g/ml, preferably 0.1-2 g/ml, and more preferably 0.1-0.8 g/ml.

In another preferred embodiment, the canagliflozin material is dissolved in the third solvent at 20-90° C.

In another preferred embodiment, before step b-1), it further comprises the following step:

b-0) the canagliflozin material is prepared as a hemihydrate crystalline form.

In another preferred embodiment, before step b-2), it further comprises the following step:

b-11) filtering insoluble substances from the solution obtained in step b-1).

In another preferred embodiment, the filtering in step b-11) is filtering by using a nylon film.

In another preferred embodiment, the pore size of the nylon film is 0.1-1 um, preferably 0.1-0.5 um, and more preferably 0.45 um.

In another preferred embodiment, the mass ratio of crystalline form W seed used in step b-2) to canagliflozin material used in step b-1) is 1:1-500, preferably 1: 1-300, and more preferably 1:1-100.

In another preferred embodiment, the crystalline form W seed of step b-2) is firstly added into a fourth solvent to obtain a third mixture, and then the second solution of step b-1) is slowly added into the third mixture, thereby crystallizing to obtain the crystalline form W in the first aspect of the present invention, wherein, the fourth solvent is selected from the group consisting of: ethyl ether, isopropyl ether, petroleum ether, methyl tert-butyl ether, n-hexane, cyclohexane, n-pentane, n-heptane, chloralkane, or combinations thereof.

In another preferred embodiment, in the third mixture, the mass concentration of the crystalline form W seed is 0.1-10 mg/ml, preferably 0.5-5 mg/ml, and more preferably 0.5-3 mg/ml.

In another preferred embodiment, the volume ratio of the third solvent to the fourth solvent is 1-10:50-1, preferably 1-8:30-1, and more preferably 1-5:15-1.

In the fourth aspect of the present invention, it provides a pharmaceutical composition, which comprises the crystalline form W in the first aspect of the present invention and a pharmaceutically acceptable carrier or excipient.

In another preferred embodiment, the carrier is selected from the group consisting of: a diluent, a binder, a disintegrator, a lubricant, or combinations thereof.

In another preferred embodiment, there is no limitation to the excipient which comprises any conventional excipient in the art.

In another preferred embodiment, the preparation forms of the pharmaceutical composition include oral solid formulations such as tablets, capsules, orally disintegrating tablets, lozenges, controlled release formulations, etc., which can be obtained by using any appropriate preparation method for corresponding dosage form.

In the fifth aspect of the present invention, it provides a use of the crystalline form W in the first aspect of the present invention or the pharmaceutical composition in the fourth aspect of the present invention in the preparation of a medicine for preventing or treating type I and II diabetes, diabetic retinopathy, diabetic neuropathy, diabetic nephropathy, hyperglycemia (postprandial), hyperinsulinemia, or diabetes complications.

In the sixth aspect of the present invention, it provides a method for preventing or treating type I and type II diabetes, diabetic retinopathy, diabetic neuropathy, diabetic nephropathy, hyperglycemia, hyperinsulinemia, or diabetes complications, which comprises a step of administering an effective dose of the crystalline form W in the first aspect of the present invention or the pharmaceutical composition in the fourth aspect of the present invention to a subject in need of.

It should be understood that in the present invention, any of the technical features specifically described above and below (such as in the Examples) can be combined with each other, thereby constituting new or preferred technical solutions which will not redundantly be described one by one herein.

DETAILED DESCRIPTION

Through extensive and intensive long research, the inventors have unexpectedly prepared a new crystalline form of canagliflozin with high purity, stable physical and chemical properties, excellent reproducibility and industrial production suitability. Based on these findings, the inventors have completed the present invention.

Terms

As used herein, terms "crystalline form W of 1-(β-D-glucopyranosyl)-4-methyl-3-[5-(4-fluorophenyl)-2-thienyl-methyl]benzene of the present invention" or "crystalline form W" are exchangeable, and each means a crystalline form whose X-ray powder diffraction pattern has 3 or more 2θ values selected from the group consisting of: 8.3±0.2°, 12.0±0.2°, 15.2±0.2°, 17.4±0.20, 17.9±0.20, and 22.8±0.2°.

As used herein, the term "onset" generally refers to the extrapolated onset temperature, which is generally regarded as the melting point of a substance.

Crystalline Form W

In the present invention, a crystalline form W of 1-(β-D-glucopyranosyl)-4-methyl-3-[5-(4-fluorophenyl)-2-thienylmethyl]benzene is provided, and the X-ray powder diffraction pattern of the crystalline form W comprises 3 or more 2θ values selected from the group consisting of: 8.3±0.2°, 12.0±0.2°, 15.2±0.2°, 17.4±0.20, 17.9±0.20, and 22.8±0.2°.

In another preferred embodiment, the X-ray powder diffraction pattern of the crystalline form W comprises 3 or more 2θ values selected from the group consisting of: 8.3°, 12.0°, 15.2°, 17.4°, 17.9°, and 22.8°.

In another preferred embodiment, the X-ray powder diffraction pattern of the crystalline form W comprises the following 2θ value: 8.3°, 12.0°, 15.2°, 17.4°, 17.9°, and 22.8°.

Typically, the X-ray powder diffraction pattern of the crystalline form W comprises 6 or more 2θ values selected from the group consisting of: 4.1±0.2°, 8.3±0.2°, 9.6±0.2°, 12.0±0.2°, 12.5±0.2°, 15.2±0.2°, 16.7±0.20, 17.4±0.20, 17.9±0.20, 20.4±0.2°, 21.5±0.2°, 22.8±0.2°, 24.3±0.2°, and 31.4±0.2°.

In another preferred embodiment, the X-ray powder diffraction pattern of the crystalline form W comprises 6 or more 2θ values selected from the group consisting of: 4.1°, 8.30, 9.60, 12.00, 12.50, 15.20, 16.70, 17.40, 17.90, 20.40, 21.50, 22.80, 24.30, and 31.4°.

In another preferred embodiment, the crystalline form W has an X-ray powder diffraction pattern as substantially shown in FIG. 1.

In another preferred embodiment, the 2θ values of the X-ray powder diffraction pattern of the crystalline form W have a deviation of ±0.5, and preferably a deviation of ±0.3, and more preferably a deviation of ±0.1.

In the present invention, the differential scanning calorimetry pattern of the crystalline form W comprises a characteristic peak in the range of 25-200° C. with an onset of approximately 80-90° C.

In another preferred embodiment, the crystalline form W has a differential scanning calorimetry pattern as substantially shown in FIG. 2.

In the present invention, the infrared absorption spectrum of the crystalline form W comprises characteristic peaks at 3326±2 cm$^{-1}$, 2928±2 cm$^{-1}$, 1647±2 cm$^{-1}$, 1411±2 cm$^{-1}$, 1358±2 cm$^{-1}$, 1323±2 cm$^{-1}$, 1280±2 cm$^{-1}$, 923±2 cm$^{-1}$, 832±2 cm$^{-1}$, 811±2 cm$^{-1}$, 707±2 cm$^{-1}$, 687±2 cm$^{-1}$, and 452±2 cm$^{-1}$.

In another preferred embodiment, the infrared absorption spectrum of the crystalline form W has characteristic peaks at 3326±1 cm$^{-1}$, 2928±1 cm$^{-1}$, 1647±1 cm$^{-1}$, 1411±1 cm$^{-1}$, 1358±1 cm$^{-1}$, 1323±1 cm$^{-1}$, 1280±1 cm$^{-1}$, 923±1 cm$^{-1}$, 832±1 cm$^{-1}$, 811±1 cm$^{-1}$, 707±1 cm$^{-1}$, 687±1 cm$^{-1}$, and 452±1 cm$^{-1}$.

In another preferred embodiment, the crystalline form W has an FTIR pattern as substantially shown in FIG. 4.

In the present invention, the TGA pattern of the crystalline form W has about 3.89% of weight loss at 25-100° C.

In another preferred embodiment, the crystalline form W has a TGA pattern W as substantially shown in FIG. 3.

In another preferred embodiment, the crystalline form is rodlike.

Preparation Method

In the present invention, it provides a preparation method of the crystalline form W of the present invention, comprising the following steps:

a-1) providing a first solution which contains a first solvent and a canagliflozin material dissolved in the first solvent, wherein the first solvent is a good solvent or a mixed solvent of the good solvent and water;

typically, the good solvent includes (but is not limited to): alcohols, ketones, esters, ethylene glycol dimethyl ether, tetrahydrofuran, acetonitrile, dimethylsulfoxide, N-methylpyrrolidone, N,N-dimethylformamide, N,N-dimethylacetamide, or combinations thereof;

a-2) slowly adding the first solution of step a-1) dropwise into a −25 to 50° C. second solvent, thereby crystallizing to obtain the crystalline form W of the present invention, wherein, the second solvent is selected from the group consisting of: water, ethyl ether, isopropyl ether, petroleum ether, methyl tert-butyl ether, n-hexane, cyclohexane, n-pentane, n-heptane, and combinations thereof.

In another preferred embodiment, the alcohols, the ketones and the esters have no particular limitation and can be any materials commonly used in the art, or can be prepared by conventional methods in the art, or can be purchased from the market.

In another preferred embodiment, the alcohol is C1-C10 alcohol, preferably is C1-C6 alcohol, and more preferably is C1-C3 alcohol.

Typically, the alcohol includes (but is not limited to): methanol, ethanol, isopropanol, or combinations thereof.

In another preferred embodiment, the alcohol is preferably isopropanol.

In another preferred embodiment, the ketone is C2-C8 ketone, preferably is C3-C5 ketone, and preferably acetone.

In another preferred embodiment, the ester is C2-C10 ester, preferably C3-C7 ester, and preferably ethyl acetate.

In another preferred embodiment, the first solvent is a mixed solvent of a good solvent and water.

In another preferred embodiment, the good solvent and water can be mixed in any ratio.

In another preferred embodiment, the volume ratio of the good solvent to water is 1-30:1, preferably 1-20:1, and more preferably 1-10:1.

In another preferred embodiment, in the first solution, the concentration of canagliflozin is 0.01-5 g/ml, preferably 0.01-2 g/ml, and more preferably 0.05-0.5 g/ml.

In another preferred embodiment, in the first solution, the concentration of canagliflozin is an unsaturated concentration.

In another preferred embodiment, the canagliflozin material is dissolved in the first solvent at 20-80° C.

In another preferred embodiment, before step a-2), it further comprises the following step:

a-11) filtering insoluble substances from the first solution.

In another preferred embodiment, the filtering in step a-11) is filtering by using a nylon film.

In another preferred embodiment, the pore size of the nylon film is 0.1-1 um, preferably 0.1-0.5 um, and more preferably 0.45 um.

In another preferred embodiment, the second solvent and the first solvent is mixed in any ratio.

In another preferred embodiment, the volume ratio of the second solvent to the first solvent is 1-5:5-1, preferably 1-5:1, and more preferably 1-4:1.

In the present invention, it also provides a preparation method of the crystalline form W of the present invention, comprising the following steps:

b-1) dissolving a canagliflozin material in a third solvent to give a second solution, wherein, the third solvent is a mixed solvent of a good solvent and water, or a mixed solvent of a good solvent and a poor solvent and water;

typically, the good solvent includes (is but is not limited to): alcohols, ketones, esters, dimethyl sulfoxide (DMSO), N-methylpyrrolidone, tetrahydrofuran, acetonitrile, N,N-dimethylformamide, N,N-dimethylacetamide, ethylene glycol dimethyl ether, or combinations thereof;

typically, the poor solvent includes (is but not limited to): ethyl ether, isopropyl ether, petroleum ether, methyl tert-butyl ether, n-hexane, cyclohexane, n-pentane, n-heptane, chloralkane, or combinations thereof;

b-2) adding a crystalline form W obtained in the present invention into the second solution, thereby crystallizing to obtain the crystalline form W of the present invention.

In the present invention, the alcohols, the ketones and the esters have no particular limitation and can be any materials commonly used in the art, or can be prepared by conventional methods in the art, or can be purchased from the market.

In another preferred embodiment, the alcohol is C1-C10 alcohol, preferably C1-C6 alcohol, and more preferably C1-C3 alcohol.

In another preferred embodiment, the alcohol is selected from the group consisting of: methanol, ethanol, isopropanol, or combinations thereof.

In another preferred embodiment, the ketone is C2-C8 ketone, preferably C3-C5 ketone, and preferably acetone.

In another preferred embodiment, the ester is C2-C10 ester, preferably C3-C7 ester, and preferably ethyl acetate.

In another preferred embodiment, the chloralkane is methylene chloride or chloroform, and preferably methylene chloride.

In another preferred embodiment, the third solvent is a mixed solvent of a good solvent and water.

In another preferred embodiment, the good solvent and water is mixed in any ratio.

In another preferred embodiment, the volume ratio of the good solvent to water is 1-50:5-1, preferably 1-30: 3-1, and more preferably 1-10:1.

In another preferred embodiment, the third solvent is a mixed solvent of a good solvent, a poor solvent and water.

In another preferred embodiment, the good solvent and poor solvent and water are mixed in any ratio.

In another preferred embodiment, in the third solvent, the volume ratio of (the good solvent+the poor solvent) to water is 1-50:5-1, preferably 1-30:3-1, and more preferably 1-10: 1.

In another preferred embodiment, in the second solution, the concentration of canagliflozin is 0.05-5 g/ml, preferably 0.1-2 g/ml, and more preferably 0.1-0.8 g/ml.

In another preferred embodiment, the canagliflozin material is dissolved in the third solvent at 20-90° C.

In another preferred embodiment, before step b-1), it further comprises the following step:

b-0) the canagliflozin material is prepared as hemihydrate crystalline form.

In another preferred embodiment, before step b-2), it further comprises the following step:

b-11) filtering insoluble substances from the solution obtained in step b-1).

In another preferred embodiment, the filtering in step b-11) is filtering by using a nylon film.

In another preferred embodiment, the pore size of the nylon film is 0.1-1 um, preferably 0.1-0.5 um, and more preferably 0.45 um.

In another preferred embodiment, the mass ratio of crystalline form W seed used in step b-2) to the canagliflozin material used in step b-1) is 1:1-500, preferably 1:1-300, and more preferably 1:1-100.

In another preferred embodiment, the crystalline form W seed of step b-2) is firstly added into a fourth solvent to obtain a third mixture, and then the second solution of step b-1) is slowly added into the third mixture, thereby crystallizing to obtain the crystalline form W of the present invention, wherein, Typically, the fourth solvent includes (is but not limited to): ethyl ether, isopropyl ether, petroleum ether, methyl tert-butyl ether, n-hexane, cyclohexane, n-pentane, n-heptane, chloralkane, or combinations thereof.

In another preferred embodiment, in the third mixture, the mass concentration of the crystalline form W seed is 0.1-10 mg/ml, preferably 0.5-5 mg/ml, and more preferably 0.5-3 mg/ml.

In another preferred embodiment, the third solvent and the fourth solvent are mixed in any ratio.

In another preferred embodiment, the volume ratio of the third solvent to the fourth solvent is 1-10:50-1, preferably 1-8:30-1, and more preferably 1-5:15-1.

Pharmaceutical Compositions and the Use Thereof

The present invention also provides a pharmaceutical composition, which comprises the crystalline form W of the present invention and a pharmaceutically acceptable carrier or excipient.

Typically, the carrier includes (but is not limited to): a diluent, a binder, a disintegrator, a lubricant, or combinations thereof.

In the present invention, the excipient is not particularly limited and can be any conventional excipient in the art.

In the present invention, the preparation forms of the pharmaceutical composition are not particularly limited, and preferably include oral solid formulations such as tablets, capsules, orally disintegrating tablets, lozenges, controlled release formulations, etc., which can be obtained by using any appropriate preparation method for the corresponding dosage form.

The present invention also provides a use of the crystalline form W of the present invention or the pharmaceutical composition of the present invention in the preparation of drugs for preventing or treating type I and II diabetes, diabetic retinopathy, diabetic neuropathy, diabetic nephropathy, hyperglycemia (postprandial), hyperinsulinemia, or diabetes complications.

The present invention also provides a method for preventing or treating type I and type II diabetes, diabetic retinopathy, diabetic neuropathy, diabetic nephropathy, hyperglycemia, hyperinsulinemia, or diabetes complications, which comprises a step of administering an effective dose of the crystalline form W of the present invention or the pharmaceutical composition of the present invention to a subject in need of.

Compared with the prior art, the present invention has the following main advantages:

(1) The crystalline form W of the present invention has high purity as well as stable physical and chemical properties.

(2) The preparation method of the crystalline form W of the present invention is simple to operate and easy to control, and possesses excellent reproducibility and industrial production suitability.

(3) The crystalline form W of the present invention has excellent powder properties, and shows good powder flowability and compressibility and is suitable for subsequent production of pharmaceutical preparations.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless otherwise defined, all professional and scientific terminology used in the text have the same meanings as known to the skilled in the art. In addition, any methods and materials similar or equal with the record content can apply to the methods of the invention. The method of the preferred embodiment described herein and the material are only for demonstration purposes.

Materials and General Test Methods

Canagliflozin materials used in the examples are oily matter which was a product prior to crystallization and obtained by reference to Example 1 in WO2008069327 by evaporating the solvent under reduced pressure.

X-ray powder diffraction instrument: Brucker D8 advance X-ray powder diffraction; radiation source: copper target ($\alpha$=1.540600 Å), scanning at room temperature; voltage: 40 kv; Current: 40 mA; starting 2θ: 2.000°, scanning range: 2.0000-50.000°; step size: 0.020°; measuring time: 12.6 seconds/step.

Differential scanning calorimetry analysis (DSC) Instrument: Q2000 from TA Instruments in US, with a range of 20-200° C., heating rate: 10° C./min, nitrogen flow rate: 50 ml/min.

Thermogravimetric analysis (TGA) Instrument: SDT Q600 from TA Instruments in US, with a range of 20-300° C., heating rate: 10° C./min, nitrogen flow rate: 60 ml/min.

Infrared spectrophotometry (FTIR) analysis instrument: Nicolet 380 Fourier transform infrared spectrometer; potassium bromide tablet method; Resolution: 4.0 cm$^1$.

EXAMPLE 1

30.0 g of canagliflozin material was added into a 100 ml ethylene glycol dimethyl ether, and the mixture was heated to 50-60° C. to dissolve the canagliflozin material. After cooling to room temperature, the mixture was filtered through a nylon film with a pore size of 0.45 um so as to remove insoluble substances. The filtrate was slowly added dropwise into 300 ml of water with stirring to precipitate solid, which was filtered and dried to give 28.3 g crystalline form W.

Results

XRPD test, DSC test, TGA test and FTIR test were carried out on the resulting crystalline form W.

FIG. 1 shows an XRPD pattern of crystalline form W prepared in Example 1. It can be seen from FIG. 1 that there are several strong peaks when 2θ values are 8.3±0.2°, 12.0±0.2°, 15.2±0.2°, 17.4±0.20, 17.9±0.20, 22.8±0.2°, and there are several weak peaks when 2θ values are 4.1±0.2°, 9.6±0.2°, 16.7±0.20, 20.4±0.2°, 21.5±0.2°, 24.3±0.2°, and 31.4±0.2°.

FIG. 2 shows a DSC pattern of crystalline form W prepared in Example 1 It can be seen from FIG. 2 that there is a single endothermic peak in the range of 25-200° C. and onset is about 80-90° C.

FIG. 3 shows a TGA pattern of crystalline form W prepared in Example 1. It can be seen from FIG. 3 that the weight loss is about 3.89% in the range of 25-100° C., which means that there is one molecule of crystallization water in the crystalline form W.

FIG. 4 shows a FTIR pattern of crystalline form W prepared in Example 1. It can be seen from FIG. 4 that there are several absorption peaks at 3326±2 cm$^{-1}$, 2928±2 cm$^{-1}$, 1647±2 cm$^{-1}$, 1411±2 cm$^{-1}$, 1358±2 cm$^{-1}$, 1323±2 cm$^{-1}$, 1280±2 cm$^{-1}$, 923±2 cm$^{-1}$, 832±2 cm$^{-1}$, 811±2 cm$^{-1}$, 707±2 cm$^{-1}$, 687±2 cm$^{-1}$, and 452±2 cm$^{-1}$.

EXAMPLE 2

50.0 g of canagliflozin material was dissolved in 150 ml isopropanol at 55° C., and the mixture was filtered through a nylon film with a pore size of 0.45 um so as to remove insoluble substances. The filtrate was slowly added dropwise into 300 ml of water at 0-5° C. with stirring to precipitate solid which was filtering and drying to give 47.6 g crystalline form W.

Results

The XRPD pattern, DSC pattern, TGA pattern and FTIR pattern of the resulting crystalline form W were substantially the same as those in Example 1.

EXAMPLE 3

10.0 g of canagliflozin material was added into 100 ml mixed solvent of methanol and water (v/v=1:1), and the mixture was heated to reflux to dissolve the canagliflozin material. After cooling to about 50° C., the mixture was filtered through a nylon film with a pore size of 0.45 um so as to remove insoluble substances. 0.1 g of crystalline form W prepared in Example 1 was added into the filtrate, the temperature was kept and stirring was conducted for 1 hour, and the temperature of the mixture was slowly lowered to room temperature. After filtering and drying, 9.8 g crystalline form W was obtained with a HPLC purity of 99.94%.

Results

The XRPD pattern, DSC pattern, TGA pattern and FTIR pattern of the resulting crystalline form W were substantially the same as those in Example 1.

EXAMPLE 4

50.0 g of canagliflozin material was dissolved in 500 ml mixed solvent of acetone and water (v/v=2:1) at 50° C., and the mixture was filtered through a nylon film with a pore size of 0.45 um so as to remove insoluble substances. 0.5 g of crystalline form W as prepared in Example 1 was added into the filtrate, stirring was conducted while the temperature of the mixture was slowly lowered to room temperature so as to precipitate solid. After filtering and drying, 48.0 g crystalline form W was obtained.

Results

The XRPD pattern, DSC pattern, TGA pattern and FTIR pattern of the resulting crystalline form W were substantially the same as those in Example 1.

EXAMPLE 5

30.0 g of canagliflozin material was dissolved into a mixed solvent of 30 ml of dimethyl sulfoxide, 30 ml of ethyl acetate and 5 ml of water at room temperature, and the mixture was filtered through a nylon film with a pore size of 0.45 um so as to remove insoluble substances. 0.3 g of crystalline form W prepared in Example 1 was added into the filtrate with slow stirring so as to precipitate solid. After filtering and drying, 28.8 g crystalline form W was obtained.

Results

The XRPD pattern, DSC pattern, TGA pattern and FTIR pattern of the resulting crystalline form W were substantially the same as those in Example 1.

EXAMPLE 6

50.0 g of canagliflozin material was dissolved into a mixed solvent of 100 ml of methanol and 10 ml of water at 60° C., and the mixture was filtered through a nylon film with a pore size of 0.45 um so as to remove insoluble substance. The filtrate was slowly dropped into 300 ml of methyl tert-butyl ether containing 0.3 g of crystalline form W with stirring so as to precipitate solid. After filtering and drying, 47.5 g crystalline form W was obtained.

Results

The XRPD pattern, DSC pattern, TGA pattern and FTIR pattern of the resulting crystalline form W were substantially the same as those in Example 1.

EXAMPLE 7

According to the preparation method disclosed in Example 1 in WO2008069327, a hemihydrate crystalline form was obtained from 10.0 g of canagliflozin material. Then the resulting crystalline form was dissolved into a mixed solvent of 50 ml of DMSO, 30 ml of dichloromethane and 3 ml of water at room temperature, and the mixture was filtered through a nylon film with a pore size of 0.45 um so as to remove insoluble substances. 0.1 g of crystalline form W prepared in Example 1 was added into the filtrate with slow stirring so as to precipitate solid. After filtering and drying, 9.3 g crystalline form W was obtained.

Results

The XRPD pattern, DSC pattern, TGA pattern and FTIR pattern of the resulting crystalline form W were substantially the same as that in Example 1.

EXAMPLE 8

Crystalline forms W of canagliflozin prepared in Examples 1-7 were suspended in water of 20° C. and 60° C. for 4 days.

Figure 5:
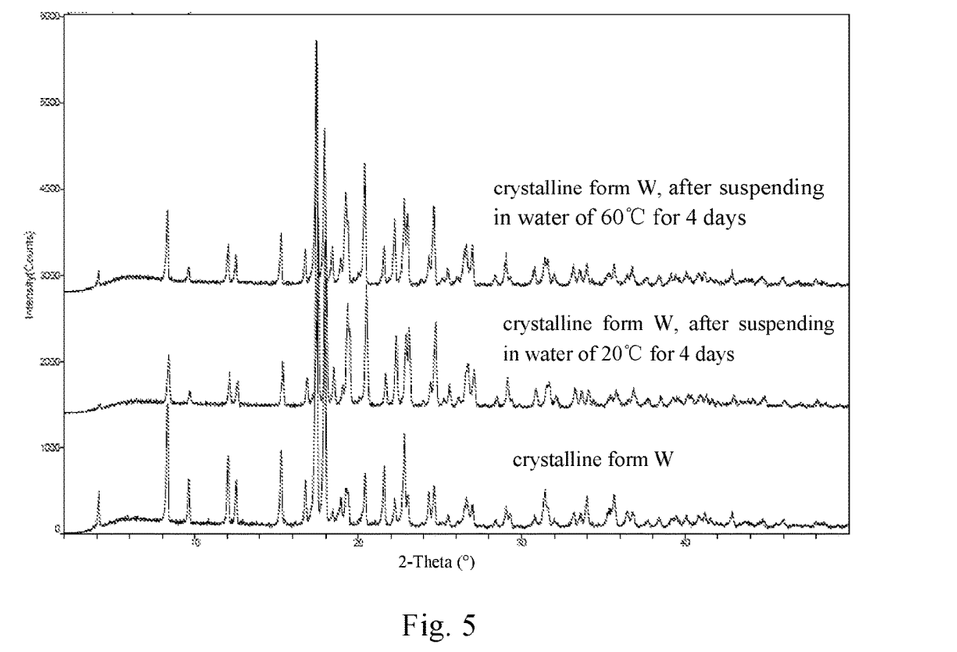
FIG. 5 shows comparative XRPD patterns of crystalline form W prepared in Example 1 of the present invention after suspending in water of 20° C. and 60° C. for 4 days.

FIG. 5 shows XRPD patterns of crystalline form W prepared in Example 1 after suspending in water of 20° C. and 60° C. for 4 days. It can be seen from FIG. 5 that the crystalline form W prepared in the present invention has excellent stability after suspending in water of 20° C. and 60° C. for 4 days.

The XRPD pattern of crystalline forms W prepared in Examples 2-7 after suspending in water of 20° C. and 60° C. for 4 days were substantially the same as FIG. 5.

EXAMPLE 9

Crystalline forms W of canagliflozin prepared in Examples 1-7 were mixed with the hemihydrate crystalline of canagliflozin (the product after crystallization) prepared in Example 1 in WO2008069327 in a ratio of 1:1, and the mixtures were suspended in water of 20° C. and 60° C. for 4 days, respectively.

Results

Figure 6:
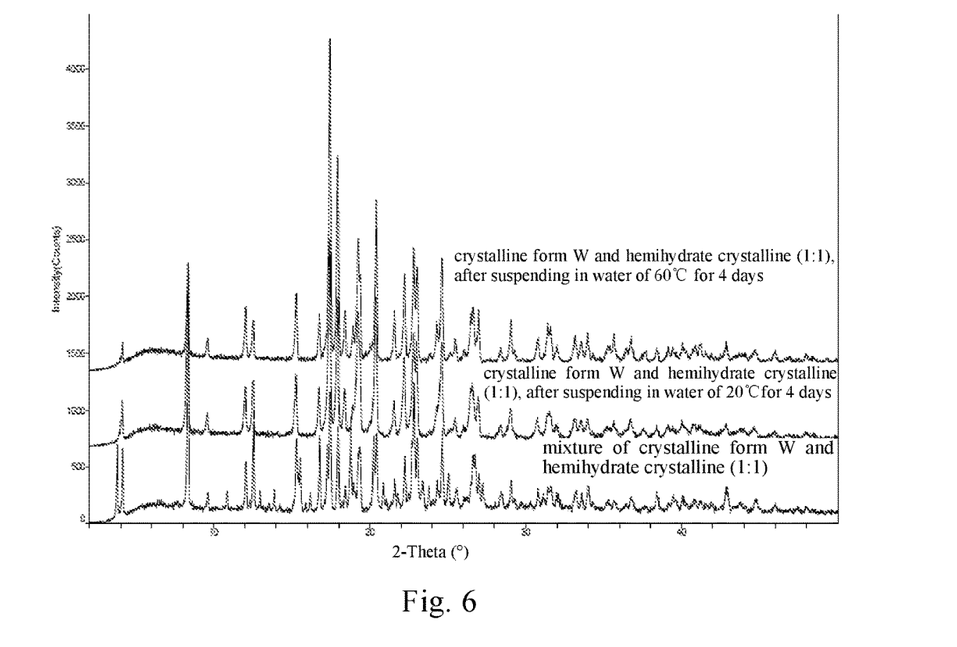
FIG. 6 shows comparative XRPD patterns of a mixture of crystalline form W prepared in Example 1 of the present invention and hemihydrate crystalline form disclosed in WO2008069327 in a ratio of 1:1 after suspending in water of 20° C. and 60° C. for 4 days.

FIG. 6 shows comparative XRPD patterns of a mixture of crystalline form W prepared in Example 1 and hemihydrate crystalline form disclosed in WO2008069327 in a ratio of 1:1 after suspending in water of 20° C. and 60° C. for 4 days. It can be seen from FIG. 6 that the hemihydrate crystalline form completely transformed into crystalline form W at last. As seen from the crystalline form competition experiments, crystalline form W of the present invention has better stability.

The XRPD patterns of a mixture of crystalline form W prepared in Examples 2-7 and hemihydrate crystalline form disclosed in WO2008069327 in a ratio of 1:1 after suspending in water of 20° C. and 60° C. for 4 days were substantially the same as FIG. 6.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. A crystalline form W of 1-(β-D-glucopyranosyl)-4-methyl-3-[5-(4-fluorophenyl)-2-thienylmethyl]benzene, wherein the crystalline form W has an X-ray powder diffraction pattern substantially as shown in FIG. 1.

2. The crystalline form W of claim 1, wherein a differential scanning calorimetry pattern of the crystalline form W comprises a characteristic peak in the range of 25-200° C. with an onset of approximately 80-90° C.

3. The crystalline form W of claim 1, wherein the crystalline form W has a differential scanning calorimetry pattern as substantially shown in FIG. 2.

4. The crystalline form W of claim 1, wherein an infrared absorption spectrum of the crystalline form W has characteristic peaks at $3326\pm2$ cm$^{-1}$, $2928\pm2$ cm$^{-1}$, $1647\pm2$ cm$^{-1}$, $1411\pm2$ cm$^{-1}$, $1358\pm2$ cm$^{-1}$, $1323\pm2$ cm$^{-1}$, $1280\pm2$ cm$^{-1}$, $923\pm2$ cm$^{-1}$, $832\pm2$ cm$^{-1}$, $811\pm2$ cm$^{-1}$, $707\pm2$ cm$^{-1}$, $687\pm2$ cm$^{-1}$, $452\pm2$ cm$^{-1}$.

5. The crystalline form W of claim 1, wherein the crystalline form W has an FTIR pattern as substantially shown in FIG. 4.

6. The crystalline form W of claim 1, wherein the TGA pattern of the crystalline form W has about 3.89% of weight loss at 25-100° C.

7. The crystalline form W of claim 1, wherein the crystalline form W has a TGA pattern W as substantially shown in FIG. 3.

8. A method for preparing a crystalline form W of claim 1, which comprises the following steps:
- a-1) providing a first solution which contains a first solvent and a canagliflozin material dissolved in the first solvent, wherein the first solvent is a good solvent or a mixed solvent of the good solvent and water;
wherein the good solvent is selected from the group consisting of: alcohols, ketones, esters, ethylene glycol dimethyl ether, tetrahydrofuran, acetonitrile, dimethylsulfoxide, N-methylpyrrolidone, N,N-dimethylformamide, N,N-dimethylacetamide, and combinations thereof; and
- a-2) slowly adding the first solution of step a-1) dropwise into a −25 to 50° C. second solvent, thereby crystallizing to obtain the crystalline form W of claim 1, wherein,
the second solvent is selected from the group consisting of: water, ethyl ether, isopropyl ether, petroleum ether, methyl tert-butyl ether, n-hexane, cyclohexane, n-pentane, n-heptane, and combinations thereof.

9. A method for preparing a crystalline form W of claim 1, which comprises the following steps:
- b-1) dissolving a canagliflozin material in a third solvent to give a second solution, wherein,
the third solvent is a mixed solvent of a good solvent and water, or a mixed solvent of a good solvent, a poor solvent and water;

wherein the good solvent is selected from the group consisting of: alcohols, ketones, esters, dimethyl sulfoxide (DMSO), N-methylpyrrolidone, tetrahydrofuran, acetonitrile, N,N-dimethylformamide, N,N-dimethylacetamide, ethylene glycol dimethyl ether, and combinations thereof;

the poor solvent is selected from the group consisting of: ethyl ether, isopropyl ether, petroleum ether, methyl tert-butyl ether, n-hexane, cyclohexane, n-pentane, n-heptane, chloralkane, and combinations thereof; and b-2) adding a crystalline form W as a seed crystal into the second solution, thereby crystallizing to obtain the crystalline form W of claim 1.

10. A pharmaceutical composition, which comprises a crystalline form W of claim 1 and a pharmaceutically acceptable carrier or excipient.

11. A method for preventing or treating type I and type II diabetes, diabetic retinopathy, diabetic neuropathy, diabetic nephropathy, hyperglycemia, hyperinsulinemia, or diabetes complications, which comprises a step of administering an effective dose of a crystalline form W of claim 1 to a subject in need of.

12. The crystalline form W of claim 1, wherein the crystalline form W is prepared by the following steps:

a-1) providing a first solution which contains a first solvent and a canagliflozin material dissolved in the first solvent, wherein the first solvent is a good solvent;

wherein the good solvent is selected from the group consisting of: ketones, ethylene glycol dimethyl ether, acetonitrile, dimethylsulfoxide, N-methylpyrrolidone, N,N-dimethylformamide, N,N-dimethylacetamide, and combinations thereof; and a-2) slowly adding the first solution of step a-1) dropwise into a −25 to 50° C. second solvent, thereby crystallizing to obtain the crystalline form W of claim 1, wherein, the second solvent is selected from the group consisting of: water, ethyl ether, isopropyl ether, petroleum ether, methyl tert-butyl ether, n-hexane, cyclohexane, n-pentane, n-heptane, and combinations thereof.

* * * * *